United States Patent [19]

Geurts et al.

[11] 4,123,438

[45] Oct. 31, 1978

[54] PROCESS FOR PREPARING 2-PYRROLIDONES

[75] Inventors: Leonardus H. Geurts, Sittard; Peter J. N. Meijer, Munstergeleen, both of Netherlands

[73] Assignee: Stamicarbon, B.V., Geleen, Netherlands

[21] Appl. No.: 829,781

[22] Filed: Sep. 1, 1977

Related U.S. Application Data

[63] Continuation-in-part of Ser. No. 784,367, Apr. 4, 1977, abandoned, which is a continuation of Ser. No. 661,784, Feb. 26, 1976, abandoned.

[30] Foreign Application Priority Data

Mar. 5, 1975 [NL] Netherlands ......................... 7502574

[51] Int. Cl.$^2$ .......................................... C07D 207/26
[52] U.S. Cl. ........................................... 260/326.5 FN
[58] Field of Search ................................ 260/326.5 FN

[56] References Cited

U.S. PATENT DOCUMENTS

| 3,095,423 | 6/1963 | Copenhauer et al. | 260/326.5 FN |
| 3,103,509 | 9/1963 | Schickh | 260/239.3 A |
| 3,644,402 | 2/1972 | Takagi et al. | 260/326.5 FN |
| 3,781,298 | 12/1973 | Davis | 260/326.5 FN |
| 4,042,599 | 8/1977 | Greene | 260/326.5 FN |

*Primary Examiner*—Donald G. Daus
*Assistant Examiner*—David E. Wheeler
*Attorney, Agent, or Firm*—Cushman, Darby & Cushman

[57] ABSTRACT

2-pyrrolidone or a substituted 2-pyrrolidone is prepared in high yields by hydrogenating succinonitrile, or an alkyl-substituted succinonitrile, at 50°–200° C. in the liquid phase, in the presence of ammonia and with a partial hydrogen pressure of about 1–50 atmospheres, then the reaction mixture is contacted with water at 100°–300° C. and the desired product recovered.

11 Claims, No Drawings

PROCESS FOR PREPARING 2-PYRROLIDONES

CROSS-REFERENCE TO RELATED APPLICATIONS

This application is a continuation-in-part of our copending application Ser. No. 784,367, filed Apr. 4, 1977, now abandoned which in turn is a continuation of application Ser. No. 661,784, filed Feb. 26, 1976, now abandoned.

BACKGROUND OF THE INVENTION

The present invention relates to a process for preparing 2-pyrrolidone which is optionally substituted. Compounds of this type are known and are useful in the preparation of polyamides, like nylon-4, and as a feedstock for preparing (poly)N-vinyl pyrrolidone.

According to published German Application 1,923,063 2-pyrrolidone can be obtained by hydrogenation of succinonitrile (1,2-dicyanoethane) at 80°-200° C. in pyridine or a similar solvent, forming 4-aminobutyronitrile and subsequently treating the aminonitrile at 200°-300° C. with water or an aqueous ammonia solution. The publication states the yield of this reaction procedure to be 72%.

We have now found that 2-pyrrolidone can be prepared from succinonitrile with a higher yield and that, in addition, using the same procedure a substituted succinonitrile can be converted with a good yield into the corresponding substituted 2-pyrrolidone.

DETAILED DESCRIPTION OF THE INVENTION

The process according to the invention for preparing 2-pyrrolidone, optionally substituted, is characterized in that the starting succinonitrile, which may be optionally substituted, is hydrogenated in the liquid phase in the presence of ammonia at a partial hydrogen pressure of between 1 and 50 atmospheres and that the resulting reaction product is then treated in the liquid phase with water at an elevated temperature. The resulting 2-pyrrolidone is then recovered from the reaction mixture.

As the starting material, apart from the succinonitrile, a substituted succinonitrile may be used such as a succinonitrile being substituted with an alkyl group having up to 4 carbon atoms in the 2nd or 3rd positions or both.

The process according to the present invention may be conducted within wide pressure ranges but preferably within the mentioned range of 1-50 atmospheres at different partial hydrogen pressures. We have found that a partial hydrogen pressure of between 15 and 25 atmospheres appears to be the most suitable in practice. During the course of the reaction, the partial hydrogen pressure may vary, however, we prefer that the partial hydrogen pressure be controlled during the hydrogenation reaction to remain about constant.

The hydrogenation may be effected at various temperatures depending upon the nature of the reactants and pressures employed. Temperatures from 50° to 200° C., preferably between 100° and 150° C., are highly suitable for carrying out the hydrogenation.

The quantity of ammonia to be present at the hydrogenation may be varied within certain practical limits. For instance, we have found that an amount of 0.5 mole of ammonia per mole of succinonitrile may be used, however, as a practical matter more than 15 moles of ammonia per mole of succinonitrile results in no particular advantage. From about 3 to about 9 moles of ammonia to every mole of succinonitrile produces a highly suitable result and thus is the preferred range. Preferably the hydrogenation is conducted in the presence of an inert solvent such as a pyridine, a pyrrolidone or toluene. By preference, a water-immiscible solvent, like toluene, is applied as inert solvent because in that case, after the hydrogenation, the reaction-mixture can be subjected to water extraction, the organic layer be recycled, and the water layer be passed directly to the hydrolysis unit. The choice of a solvent, if used, is not critical to the novel process here disclosed so long as the solvent remains inert and does not enter into the reaction. The experienced operator will have no difficulty in selecting the appropriate solvent.

Several known catalysts are useful in the hydrogenation reaction such as Raney nickel, Raney cobalt, palladium on carbon, and nickel on silicon dioxide. The amount of catalyst is an amount customarily used for hydrogenations.

The treatment with water of the reaction product obtained from the hydrogenation reaction may be carried in the presence or absence of ammonia depending on operating conditions. Different temperatures may then be chosen, for instance between 100° and 300° C. for the water treatment step. We prefer to operate within the temperature range of about 150°-250° C. because at such a temperature the required efficiency can be achieved at a sufficiently rapid reaction rate and at a pressure which is not excessively high. The amount of water used in this treatment is usually 1-20 moles, preferably 5-15 moles, per mole of succinonitrile.

The process according to the present invention may be conducted either continuously and batchwise, and is further illustrated in more detail in the following examples. Unless otherwise indicated, all parts and percents are by weight.

Comparative examples are designated with letters while examples according to the present invention are indicated by numerals.

EXAMPLE 1

Succinonitrile (40 g), pyridine (337 g), and ammonia (50 g) are introduced into a 1-liter autoclave, which is provided with a stirrer, a heating jacket and a hydrogen supply. The autoclave is brought to a temperature of 120° C., whereupon pyridine (60 g) and Raney nickel catalyst (4 g) are forced into the autoclave with the aid of hydrogen; the partial hydrogen pressure is set at 20 atmospheres.

Next, the stirrer is started and the reaction commences. During the hydrogenation, the partial hydrogen pressure is maintained at 20 atmospheres by supplying fresh hydrogen as required.

After about 15 minutes, the hydrogenation reaction is completed and the catalyst is removed from the reaction mixture by filtration. After cooling, the filtrate is transferred, together with water (175 g), to a steel tube and heated for 2 hours at 210° C. for the hydrolysis of the filtrate.

Following the hydrolysis the resulting reaction mixture is analyzed gaschromatographically, which shows that succinonitrile is no longer present and that 36.5 g of 2-pyrrolidone have formed, which corresponds with a yield of 86% of the yield theoretically possible.

By distillation of the resulting reaction mixture at 133° C. and a pressure of 12 mm Hg, 2-pyrrolidone (34.4 g) having a purity of 99% is obtained.

Comparative Example A

Example 1 is repeated but without addition of ammonia. Gaschromatographic analysis of the reaction mixture shows that the mixture contains 28.9 g of 2-pyrrolidone; yield 68%.

Comparative Example B

Example 1 is repeated, the difference being that the partial hydrogen pressure is set at 100 atmospheres (5 times that of Example 1). Gaschromatographic analysis shows that 26.0 g of 2-pyrrolidone are present in the reaction mixture; yield 61%.

EXAMPLE 2

Example 1 is repeated, however, the hydrogenation is carried out at 100° C. and in a reaction time of 20 minutes. Gaschromatographic analysis of the reaction mixture shows a yield of 33.6 g of 2-pyrrolidone; yield 79%.

EXAMPLE 3

Example 1 is repeated, however, the hydrogenation is carried out at 140° C. and in a reaction time of 10 minutes. Gaschromatographic analysis of the reaction mixture shows that it contains 33.2 g of 2-pyrrolidone; yield 78%.

EXAMPLE 4

Example 1 is repeated, this time using as the starting material α-methylsuccinonitrile (47 g). The reaction mixture is worked up by distillation and contains 4-methylpyrrolidone-2 (14.1 g) and 3-methylpyrrolidone-2 (24.0 g). The total yield amounts to 77% of the yield theoretically possible.

EXAMPLE 5

Example 1 is repeated, however, the hydrogenation is carried out with the use of toluene as solvent. Gaschromatographic analysis of the reaction mixture shows a yield of 35.3 g of 2-pyrrolidone; yield 83%.

EXAMPLE 6

Example 1 is repeated, this time using as the starting material 1.2-dicyano-4-methylpentane (68 g). The reaction mixture is worked up by distillation and contains 3-isobutylpyrrolidone-2 (42.9 g) and 4-isobutylpyrrolidone-2 (12.8 g). The total yield amounts to 79% of the yield theoretically possible.

EXAMPLE 7

Example 1 is repeated, however, the heating of the filtrate with water in the steel tube is carried out for 3.5 hours at 150° C. Gaschromatographic analysis of the reaction mixture shows that it contains 35.7 g of 2-pyrrolidone; yield 84%.

EXAMPLE 8

Succinonitrile (200 g), toluene (1800 g), ammonia (170 g) and 20 g Raney nickel catalyst are introduced into a 5-liter autoclave, which is provided with a stirrer and a heating jacket. The partial hydrogen pressure is set at 20 atmospheres, the stirrer started and the mixture heated. The reaction commence at 55° C. During the hydrogenation, the partial hydrogen pressure is maintained at 20 atmospheres by supplying fresh hydrogen as required. Because of the heat of reaction the temperature of the reaction mixture increases to 86° C. After about 10 minutes of reaction at about 86° C. the consumption of hydrogen and the temperature decreases. The catalyst is then removed from the reaction mixture by filtration. After cooling, the filtrate is extracted with water (450 g) and the aqueous solution obtained transferred into a 1-liter autoclave, which is provided with a stirrer and a heating jacket. The mixture is then heated, with stirring, to a temperature of 200° C. After stirring for a half hour at 200° C. the reaction mixture is cooled and analyzed gaschromatographically. The mixture contains 6.2 g of succinonitrile and 174.3 g of 2-pyrrolidone, which corresponds with a yield of 83% of the yield theoretically possible.

We claim:

1. In a process for the preparation of 2-pyrrolidone comprising the steps of hydrogenating 1,2-dicyanoethane and then hydrolyzing the reaction product by treatment with water at an elevated temperature and recovering the 2-pyrrolidone product, the improvement comprising conducting the hydrogenation step:
   (1) at a temperature of about 50°–200° C.,
   (2) in the liquid phase,
   (3) in the presence of ammonia, and
   (4) at a partial hydrogen pressure of about 1–50 atmospheres,
and thereafter conducting the hydrolysis step at a temperature of about 100°–300° C.

2. The process according to claim 1 wherein the hydrogenation step is conducted at a partial hydrogen pressure of between 15 and 25 atmospheres.

3. The process according to claim 1 wherein the hydrogenation is carried out at a partial hydrogen pressure which is substantially constant.

4. The process according to claim 1 wherein the hydrogenation is carried out in a water-immiscible solvent.

5. A process for the preparation of 2-pyrrolidone or a 2-pyrrolidone monosubstituted in the 3 or 4 position or disubstituted in the 3 and 4 position with an alkyl group of 1 to 4 carbon atoms comprising the steps of (a) contacting under hydrogenation conditions 1,2-dicyanoethane or a $C_1$–$C_4$ alkyl 1 or 2 mono- or 1 and 2 di-substituted 1,2-dicyanoethane at a temperature of about 50°–200° C. in the liquid phase, in the presence of ammonia and at a partial hydrogen pressure of about 1–50 atmospheres, then (b) hydrolyzing the reaction product of step (a) with water in the liquid phase at a temperature of about 100°–300° C., and thereafter (c) recovering the 2-pyrrolidone or said alkyl-substituted 2-pyrrolidone from the reaction mixture.

6. The process according to claim 5 wherein 1,2-dicyano-1-methylethane is the starting material.

7. The process according to claim 5 wherein 1.2-dicyano-4-methylpentane is the starting material.

8. The process according to claim 5 wherein the hydrogenation is carried out in a water-immiscible solvent.

9. The process according to claim 1 wherein the hydrolysis step is conducted at 150°–250° C.

10. The process according to claim 1 wherein the hydrogenation step is conducted at 100°–150° C.

11. In a process for the preparation of 2-pyrrolidone comprising the steps of (a) hydrogenating 1,2-dicyanoethane and thereafter (b) hydrolyzing the reaction product by treatment with water at an elevated temperature and then recovering the 2-pyrrolidone product,
   the improvement in the hydrogenation step which consists of conducting said step:
   (1) at a temperature of about 50°–200° C.,
   (2) in the liquid phase,
   (3) in the presence of ammonia, and
   (4) at a substantially constant partial hydrogen pressure of about 15–25 atmospheres,
and thereafter conducting the hydrolysis step at a temperature of about 100°–150° C.

* * * * *